US006908611B2

(12) United States Patent
Cruz et al.

(10) Patent No.: US 6,908,611 B2
(45) Date of Patent: Jun. 21, 2005

(54) COMBINATION THERAPIES USING VITAMIN B12 AND INTERFERON FOR TREATMENT OF VIRAL, PROLIFERATIVE AND INFLAMMATORY DISEASES

(75) Inventors: Tony Cruz, Toronto (CA); Aleksandra Pastrak, Toronto (CA)

(73) Assignee: Transition Therapeutics Inc., Ontario (CA)

( * ) Notice: Subject to any disclaimer, the term of this patent is extended or adjusted under 35 U.S.C. 154(b) by 0 days.

(21) Appl. No.: 10/167,765

(22) Filed: Jun. 11, 2002

(65) Prior Publication Data

US 2003/0086901 A1 May 8, 2003

Related U.S. Application Data

(63) Continuation-in-part of application No. 09/908,298, filed on Jul. 17, 2001, now abandoned, and a continuation-in-part of application No. 09/971,068, filed on Oct. 3, 2001, now abandoned.
(60) Provisional application No. 60/297,514, filed on Jun. 11, 2001, provisional application No. 60/327,700, filed on Oct. 5, 2001, provisional application No. 60/334,535, filed on Dec. 3, 2001, and provisional application No. 60/366,539, filed on Mar. 25, 2002.

(51) Int. Cl.$^7$ .................... A61K 38/21; A61K 45/00; A61K 31/714; C07K 14/00
(52) U.S. Cl. .................... 424/85.4; 424/85.1; 424/85.6; 424/85.7; 530/351; 514/52
(58) Field of Search ............................ 424/85.1, 85.4, 424/85.6, 85.7; 530/351; 514/52

(56) References Cited

U.S. PATENT DOCUMENTS

| | | | |
|---|---|---|---|
| 5,565,558 A | 10/1996 | McCully | |
| 5,574,018 A | 11/1996 | Habberfield et al. | |
| 5,716,941 A | 2/1998 | Rabinoff | |
| 5,716,946 A | 2/1998 | DeLuca et al. | |
| 5,837,822 A | 11/1998 | Gallatin et al. | |
| 5,846,526 A | 12/1998 | Cummins | |
| 5,858,980 A | 1/1999 | Weiner et al. | |
| 5,888,511 A | 3/1999 | Skurkovich et al. | |
| 5,948,764 A | 9/1999 | Guar et al. | |
| 5,958,409 A | 9/1999 | Turk et al. | |
| 6,036,957 A | 3/2000 | Weiner et al. | |
| 6,121,249 A | 9/2000 | Weissman et al. | |
| 6,143,866 A | 11/2000 | Brewer et al. | |
| 6,184,223 B1 | 2/2001 | Kahn et al. | |
| 6,752,986 B2 * | 6/2004 | Bauer et al. | ............... 424/85.6 |

FOREIGN PATENT DOCUMENTS

| | | |
|---|---|---|
| WO | WO 98/45327 | 10/1998 |
| WO | WO 99/13904 | 3/1999 |
| WO | WO 99/16791 | 4/1999 |
| WO | WO 01/12170 A2 | 2/2001 |
| WO | WO 01/28592 A1 | 4/2001 |

OTHER PUBLICATIONS

Johnson et al., Scientific American, May, 1994, pp. 68–75.*
Iigo Masaaki et al., "Markedly induced asialoGM1+CD8+ T cell production and enhancement of antimetastatic activity by interferon beta with folic or folinic acid", XP002227203 abstract, Cancer Immunology Immunotherapy, vol. 44, No. 2, 1997, pp. 65–69, ISSN: 0340–7004.
R. Medenica et al., "Vitamin B–12, A Positive Stimulator of Interferon Activity", Cancer Immuno–Biology Laboratory and Adolph Coors Clinic of Immunoregulation, Hilton Head Island, SC, abstract; 1995.
Francisco Hernandez et al., "Interferon Alpha–2B and Hydroxocobalamine in Epidemic Neuropathy," Biotechnologia Aplicada, vol. 12, No. 3, 1995, pp. 191–192.
Database Biosis 'Online!, Biosciences Information Service, Philadelphia, PA, US; 1982, Myasischeva N V et al., "Anti Tumor Efficiency of Methotrexate in Combination With Cobalamin Derivatives", Database accession No. PREV198477036851, XP002214761, abstract & Eksperimental'Naya Onkologiya, vol. 4, No. 5, 1982, pp. 29–33, ISSN: 0204–3564.
Database Biosis 'Online! Biosciences Information Service, Philadelphia, PA, US; 2000; Pinson Patrick R et al., "Synthesis, protein binding, and cellular uptake of doxorubicin–cobalamin bioconjugates." Database accession No. PREV200000222560; XP002157413; abstract & Abstracts of Papers American Chemical Society, vol. 219, No. 1–2, p. MEDI 82 219$^{th}$ Meeting of the American Chemical Society; San Francisco, California USA; Mar. 26–30, 2000; ISSN 0065–7727.
Jun–ichi Kira et al., "Vitamine B12 Metabolism and Massive–Dose Methyl Vitamin B12 Therapy in Japanese Patients with Multiple Sclerosis," Internal Medicine, Japanese Society of Internal Medicine, Tokyo, Japan, vol. 33, No. 2, Feb. 1, 1994, pp. 82–86, XP 000650481, ISSN: 0918–2918, abstract.
Prisms (Prevention of Relapses and Disability by Interferon β–1a Subcutaneously in Multiple Schlerosis), "Randomized double–blind placebo–controlled study of interferon β–1a in relapsing/remitting multiple schlerosis", Lancet, vol. 352, No. 9139, Nov. 7, 1998, pp. 1498–1504, XP004265722, ISSN: 0140–6736, abstract.
Amit, et al., "Molecular Pathogenesis of Multiple Sclerosis", J. Immunol, 100:252–259, (1999).
Barron, K., et al., "Multiple Sclerosis", Rakel, R., Ed. 1995, Conn's Current Gherapy, WB Saunders Company, USA, pp. 732–734.

(Continued)

Primary Examiner—Janet Andres
(74) Attorney, Agent, or Firm—Fish & Richardson P.C.

(57) ABSTRACT

Pharmaceutical compositions for treating viral, proliferative and inflammatory diseases are disclosed comprising an amount of pharmaceutically acceptable vitamin B12 compound in combination with an interferon compound. Vitamin B12 compounds are administered separately, simultaneously or in combination with interferon compounds to provide an enhanced therapeutic effect for treating viral, proliferative and inflammatory diseases.

17 Claims, 3 Drawing Sheets

OTHER PUBLICATIONS

Brod, SA, et al., "Combination Therapy will Glatiramer Acetate Copolymer–1 and Type I Interferon (interferon–alpha) Does Not Improve Experimental Autoimmune Encephalomyelitis", *Annals of Neurology*, 47(1), pp. 127–131 (2000).

Cabrera–Gomez, et al., Alpha Interferon in the Treatment of Multiple Sclerosis. Update and Experience in Cuba, *Rev. Neuro*, 28:849–858, (1999).

Cao, et al., "Inhibition of Experimental Allergic Encephalomyelitis in the Lewis Rat by Paclitaxel", *J. Neuroummunol.*, 108:103–111, (2000).

Chofflon, et al., "Recombinant Human Interferon Beta In Relapsing–Remitting Multiple Sclerosis: A Review of the Major Clinical Trials", *European J. Neur.*, 7:369, (2000).

Chou, et al., "Quantitative Analysis of Dose–Effect Relationships: The Combined Effects of Multiple Drugs or Enzyme Inhibitors", *Advances in Enzyme Regulation*, vol. 22, pp. 27–55 (1984).

Deisenhammer, et al., "Bioavailability of Interferon–Beta–1B in MS Patients with without Neutralizing Antibodies", *Neurology*, 52(6), pp. 1239–1243 (1999).

Durelli, et al., "Chronic Systemic High–Dose Recombinant Interferon Alfa–2a Reduces Exacerbation Rate, MRI Signs of Disease Activity and Lymphocyte Interferon Gamma Production in Relapsing–Remitting Multiple Sclerosis", *Neuro*, 44 (3 Pt 1): 406–413, (1994).

Fine, et al., "A Phase I Trial of a New Recombinant Human Beta–Interferon (BF9015) For the Treatment of Patients with Recurrent Gliomas", *Clinical Cancer Research*, 3(3), pp. 1–7 (1997).

Hall, et al., "Hydroxycabalamin/Sodium Thiosulfate as a Cyanide Antidote", *J. of Emergency Medicine*, 5(2), pp. 115–121 (1987).

Ide, H. et al., "Clinical Usefulness of Intrathecal Injection of Methylcobalamin in Patients with Diabetic Neuropathy", *Clin. Ther.*, 9:183–187, (1987).

Johnson, et al., "Copolymer 1 Reductes Relapse Rate and Improves Disability in Relapsing–Remitting Multiple Sclerosis: Results of Phase III Mulicenter, Double–Blind, Placebo–Controlled Trial", *Neuro*, 45:1268–1276, (1995).

Johnson, et al., "Extended use of Glatiramer Acetate (Copaxone) is Well Tolerated and Maintains Its Clinical Effect on Multiple Sclerosis Relapse Rate and Degree of Disability", *Neuro*, 50:701–708, (1998).

Lott, et al., "Vitamin B12 and Hepatitis C: Molecular Biology and Human Pathology", *Mol. Biol. and Human Path.*, Proceedings of National Academy of Sciences, 98(9), pp. 4916–4921 (2001).

Mastronardi, et al., "Demyelination in a Transgenic Mouse: A Model for Multiple Sclerosis", *J. Neuro. Res.*, 36:315–324, (1993).

Mattner, et al., "Inhibition of Th1 Development and Treatment of Chronic–Relapsing Experimental Allergic Encephalomyelitis by a Non–Dihydroxyvitamin D3", *European J. Immunol.*, 30:498–508, (2000).

Miller, et al., "Magnetic Resonance In Monitoring the Treatment of Multiple Sclerosis", *Ann. Neurol.*, 36:Supp:S91–4, (1994).

Myhr, et al., Interferon–alpha2a Reduces MRI Disease Activity in Relapsing–Remitting Multiple Sclerosis: Norwegian Study Group on Interferon–alpha in Multiple Sclerosis, *Neuro*, 23:52(5):1049–1056, (1999).

Nataf, et al., "Dihydroxyvitamin D3 Exerts Regional Effects in the Central Nervous System During Experimental Allergic Encephalomyelitis", *J. Neuro Exp. Neuro*, 55:904–914, (1996).

Nishizawa, et al., "Effects of Methylcobalamin on the Proliferation of Androgen–Sensitive or Estrogen–Sensitive Malignant Cells in Culture and In Vivo", *International J. of Vitamin Nutrition Research*, 67(3), pp. 164–170 (1997).

Norvedt, et al., "Type I Interferons and the Quality of Life of Multiple Sclerosis Patients. Results from a Clinical Trial on Interferon alfa–2a", *Multiple Scler.*, 5:317–322, (1999).

O'Connor, et al., "A Phase 1 Study of Micellar Paclitaxel in the Treatment of Secondary Progressive Multiple Sclerosis", *Ann. Neurol*, 46:470, (1999).

Polman, et al., "Drug Treatment of Multiple Sclerosis", *BMJ*, 321:490–494, (2000).

Pouly, et al., "Multiple Sclerosis and the Central Nervous System Demyelination", *J. Autoimmu.*, 13:297–306, (1999).

Poydock, et al., "Inhibiting Effect of Vitamins C and B12 on the Mitotic Activity of Ascites Tumors", *Experimental and Cellular Biology*, vol. 47, pp. 210–217 (1979).

Poydock, et al., "Mitogenic Inhibition and Effect of Survival of mice Bearing L1210 Leukemia Using a Combination of Dehydroascorbic Acid and Hydroxycobalamin", *Am. Journal of Clinical Oncology*, 8(3), pp. 266–269 (1985).

Rudick, et al., "Disease–Modifying Drugs for Relapsing–Remitting Multiple Sclerosis and Future Directions for Multiple Sclerosis Theraputics", *Arch. Neuro.*, 56:1079–1084, (1999).

Rudick, et al., "Drug Therapy: Management of Multiple Sclerosis", *NEJM*, 337:1604–1611, (1997).

Sakane, et al., "Effects of Methyl–B12 on the In Vitro Immune Functions of Human Lymphocytyes", *J. of Clinical Immunology*, 2(2), pp. 101–109 (1982).

Shimizu, et al., "Experimental Study of Anti–tumor Effect of Methyl–B12", *Oncology*, 44(3), pp. 169–173 (1987).

Steinman, et al., "From Treatment of Experimental Allergic Encephalmyelitis to Clinical Trials in Multiple Sclerosis", *Immunol. Ser.*, 59:253–60, (1993).

Tamura, et al., "Immunomodulation by Vitamin B12: Augmentation of CD8+ T Lymphocytes and Natural Killer (NK) Cell Activity in Vitamin B12–Deficient Patients by Methyl–B12 Treatment", *Clinical and Experimental Immunology*, 116(1), pp. 28–32 (1999).

Tselis, et al., "Multiple Sclerosis: Therapeutic Update", *Arch. Neuro.*, 56:277–280, (1999).

Tsao, et al., "Cytotoxic Activity of Cobalamine Cultured Malignant and Nonmalignant Cells", *Pathobiology*, vol. 58, pp. 292–296 (1990).

Watanabe, et al., "Ultra–high Dose of Methylcobalamin Promotes Nerve Regeneration in Experimental Acrylamide Neuropathy", *J. Neurol. Sci.*, 122:140–143, (1994).

Weinberg, et al., "Inhibition of Productive Human Immunodeficiency Virus–1 Infection by Cobalamins", *Blood*, 86(4), pp. 1281–1287 (1995).

Weinberg, et al., "Inhibition of HIV–1 Integrase and Integration of HIV–1 DNA Into Cellular DNA", *Biochem. Biophys. Res. Communications*, 246(2), pp. 393–397 (1998).

Weinstock–Guttman, et al., "What is New in the Treatment of Multiple Sclerosis?", *Drugs*, 59:401–410, (2000).

Xu, et al., "Dendritic Cell–Derived Nitric Oxide is Involved in IL–4–Induced Supression fo Experimental Allergic Encephalomyelitis (EAE) in Lewis Rats", *Clin. Exp. Immunol*, 118:115–121, (1999).

Yong, et al., "Interferon Beta in the Treatment of Multiple Sclerosis—Mechanisms of Action", *Neuro*, 51:682–689, (1998).

* cited by examiner

Figure 1. Effect of B12, interferon-beta and the synergistic combination of vitamin B12 and interferon-beta on clinical scores in ND4 mouse model Figure 2. Effect of B12, interferon-beta and the combination of B12 and interferon-beta on clinical scores in EAE mouse model Legend: EAE Untreated: control; B12: Vitamin B12 treated; MIF5000: Mouse Interferon-beta treated; MIF5000 + B12: Mouse Interferon-beta and Vitamin B12 treated.)

Figure 3. GFAP staining in brain sections from normal, ND4 untreated animals, interferon beta treated ND4 animals, and interferon-beta and vitamin B12 treated ND4 animals.

Anti-GFAP

ND INFLAMMATORY DISEASES

COMBINATION THERAPIES USING VITAMIN B12 AND INTERFERON FOR TREATMENT OF VIRAL, PROLIFERATIVE AND INFLAMMATORY DISEASES

CROSS-REFERENCE TO RELATED APPLICATIONS

This application claims benefit of U.S. Provisional Patent Applications Ser. Nos.: 60/297,514 (filed Jun. 11, 2001); 60/327,700 (filed Oct. 5, 2001); 60/334,535 (filed Dec. 3, 2001); and 60/366,539 (filed Mar. 25, 2002). It is a continuation-in-part of U.S. patent application Ser. Nos. 09/908,298 (filed Jul. 17, 2001) now abandoned and 09/971,068 (filed Oct. 3, 2001) now abandoned. The disclosure of each of the above applications is incorporated herein by reference in its entirety.

FIELD OF THE INVENTION

The present invention provides pharmaceutical compositions and methods of use for the treatment of viral, inflammatory or proliferative diseases with a vitamin B12 compound in combination with an interferon compound.

BACKGROUND OF THE INVENTION

Review of Viral, Inflammatory and Proliferative Diseases

Diseases and disorders that have significant inflammatory, viral and/or proliferative components are widespread and affect millions of people worldwide. Selected examples of inflammatory, viral and/or proliferative diseases include multiple sclerosis, diabetes, restenosis, cancer, hepatitis B, hepatitis C, HIV/AIDS and genital warts. These types of diseases share common disease processes and as a result often share or possess related/common therapies.

Viral Diseases

Viruses are potent infectious pathogenic agents that cause important functional alterations of the invaded cells, often resulting in cellular death. It is generally acknowledged that the cell injury in viral diseases includes not only direct damages inflicted by the proliferation of viruses but also various immunologic reactions elicited by infection with viruses. The consequences of a viral disease depend upon several viral and host factors such as the quantity of infecting viral particles, the speed of viral multiplication and spread, the impact on cell functions, the host's secondary responses to the cellular injury, and both the immunologic and the non-specific defenses of the host. In general, the effects of a viral disease include asymptomatic infections, both acute and chronic clinical diseases and induction of various types of cancers. One example of a well known viral disease is viral hepatitis infection which results in chronic or acute inflammation of the liver and can lead to hepatocellular carcinoma in some cases. To date, there are several types of hepatitis viruses that have been identified including hepatitis viruses A, B, C, D, E and G; such viruses are prevalent among the population. For instance, it has been estimated by Liver Foundation International that there are more than 520 million individuals worldwide that suffer from either hepatitis B or hepatitis C.

Inflammatory Diseases

Inflammatory diseases are a class of diseases and disorders that are characterized by the influx of certain cell types and mediators, the presence of which can lead to tissue damage and sometimes death. Inflammatory diseases trigger what is known as the inflammatory cascade, a complex process that involves the triggering of immunological response, the release of chemokines, cytokines and toxic agents by the activated cells, the up-regulation of cell surface adhesion molecules and trans-endothelial cell migration. Typically, inflammation occurs as a defensive response to invasion of the host by foreign material, bacteria or to mechanical trauma, toxins and neoplasia. Autoimmune responses by intrinsic stimulation also can induce inflammatory responses.

One example of inflammatory disease is multiple sclerosis ("MS"). MS is a multi-factorial inflammatory disease of the human central nervous system resulting in the slowing of electrical conduction along the nerve. It is estimated that close to a third of a million people in the United States have MS. MS is believed to result from inflammation and breakdown in the myelin surrounding the nerve fibers of the central nervous system. The disease is characterized by an increase in the infiltration of inflammatory cells, loss of oligodendrocytes, and increased gliosis (astrocyte hypertrophy and proliferation). (For review see Amit et al., 1999; Pouly et al., 1999; Steinman et al., 1993; Miller, 1994).

Proliferative Diseases

Cancer is the most well known proliferative disease. Specifically, cancer is a generic term representing a collection of diseases arising from mutations of key molecules that regulate cell proliferation, invasion, and metastasis. The ability of tumor cells to metastasize involves deregulation via overproduction or mutation of genes that allow cells to invade out of the tissue of origin, survive in a contact-independent manner, escape immune recognition, lodge at a distant site, then invade to a suitable place within the new tissue and grow there. The molecules that are commonly involved in tumor initiation, progression and metastasis include adhesion molecules, growth factor receptors, factors regulating the cytoskeleton, master switches regulating cell cycle, proliferation repressor genes, proteases and transcription factors. The ability of most tumors to kill is directly related to their capacity to invade and ultimately to metastasize.

Viral, Inflammatory and Proliferative Diseases Share Common Disease Processes

There are several classes of molecules and disease processes that are common to viral, inflammatory, and proliferative diseases. These include elevated expression of adhesion molecules, cytokines and matrix metalloproteinases, increased cell proliferation and migration, increased inflammatory cell activation and infiltration, increased angiogenesis, and increased tissue destruction and dysfunctional matrix remodeling. Consequently, compounds for the treatment of these diseases are aimed at altering the immune system, cell proliferation, cell adhesion and migration, cytokine levels or activities or viral replication.

Interferons

Interferons are multi-functional cytokines that are capable of producing pleitrophic effects on cells, such as inhibition of virus replication (anti-viral effects), inhibition of cell proliferation (anti-proliferative effects) and inhibition of inflammation (anti-inflammatory effects). Because of these cellular responses to interferons, interferon-alpha and interferon-beta have been found to be clinically useful in the treatment of viral, proliferative and inflammatory diseases such as multiple sclerosis, hepatitis B/C and a number of cancers. Interferon therapies may also have potential use for the treatment of other inflammatory diseases, viral diseases and proliferative diseases.

Need for Enhancing Compounds to Decrease Side Effects

Although interferon compounds are used or potentially can be used to treat inflammatory, viral and proliferative diseases, these compounds have many undesirable side effects, which are exacerbated at high doses. These include local injection reactions, flu-like syndrome and depression. Accordingly, some patients are unable to tolerate the doses needed to achieve a therapeutic effect.

In addition, although many anti-viral, anti-inflammatory or anti-proliferative compounds may have shown promise in vitro against inflammatory, viral, or proliferative diseases, very high doses may be required in vivo; such doses often being toxic or causing severe side effects. Therefore, the limitation of these therapies may be in using sufficient levels of the compound to achieve maximal efficacy in the absence of side effects.

Thus, compounds that can be combined with anti-viral, anti-proliferative or anti-inflammatory compounds to increase effectiveness of treatments for inflammatory, viral or proliferative diseases are necessary. In addition, compounds that can reduce the doses and/or reduce frequency of administration to reduce side effects and to maintain or improve efficacy are necessary.

For example, a compound that can improve efficacy of interferon-beta in the treatment of MS would potentially reduce the amount and/or frequency of interferon-beta administration, reducing side effects induced by interferon-beta and possibly reducing the occurrence of neutralizing antibodies to interferon-beta in MS patients.

Neutralizing antibodies to interferon-beta occur in about one third of MS patients treated with interferon-beta and are positively correlated with a loss of therapeutic efficacy of interferon-beta Deisenhammer et al., 1999).

In addition, said compounds could not only enhance the efficacy in current or potential anti-viral, anti-proliferative or anti-inflammatory therapies but could also broaden use of these therapies into many other inflammatory, proliferative and viral diseases.

There have been reports of other therapeutic agents being tested in combination with interferon for treatment of inflammatory diseases such as multiple sclerosis. However, these combination therapies have resulted in limited efficacy or no reduction in side effects. For example, combination therapy comprising copaxone and interferon-alpha did not improve clinical scores in EAE-treated mouse (Brod et al., 2000). While novantrone, an anti-proliferative drug, is currently being tested in clinical trials for combination therapy with interferon-beta, novantrone is known to have a significant side effect profile including serious cardiac toxicity. Novantrone is restricted in its use because the risk of heart disease increases with the cumulative dose. According to the Food and Drug Administration, patients with MS should ordinarily not receive more than 8 to 12 doses of novantrone, administered over two to three years.

Accordingly, there is a need to develop therapies for viral, inflammatory or proliferative diseases that result in sufficient levels of anti-viral, anti-inflammatory and anti-proliferative compounds to achieve maximal efficacy with minimal side effects. There is a need to develop anti-viral, anti-inflammatory and anti-proliferative combination therapies for the treatment of viral, inflammatory or proliferative diseases wherein the combined elements have an enhancing therapeutic effect, while minimizing side effects.

Vitamin B12

Vitamin B12 is a cobalt-containing B complex vitamin that has various effects on biological processes in vivo. Vitamin B12 has a well-elucidated family of analogues and conjugates. Vitamin B12 compounds have been known to be involved in metabolic processes; and deficiency of vitamin B12 has been known to provoke pernicious anemia and neurological disorders. It is a co-factor essential in the metabolic pathway leading to synthesis of DNA, cell division, as well as cellular metabolism. Biochemical evidence suggests that vitamin B12 compounds may up-regulate gene transcription and thereby protein synthesis (Watanabe et al, 1994). It has been also suggested that vitamin B12 compounds play an important role in immune system regulation (Tamura et al, 1999, Sakane et al, 1982).

Specifically, vitamin B12 compounds have been suggested to possess some or limited anti-viral (Weinberg et al, 1995, 1998, Lott et al, 2001, Poydock, 1979, Tsao et al., 1990), anti-proliferative (Nishizawa et al, 1997, Shimizu, 1987, Poydock et al., 1979, 1985) and anti-inflammatory activities (U.S. Pat. No. 5,508,271, U.S. Pat. No. 5,964,224, U.S. Pat. No. 5,716,941) on their own. Vitamin B12 has also been tried in combination with other therapeutic agents (EP Patent # 0835660, U.S. Pat. No. 6,096,737) for the treatment of specific inflammatory diseases or proliferative diseases. However, to date, there has been no scientific evidence demonstrating an enhanced therapeutic effect of vitamin B12 in combination with interferon compounds for treatment of viral, inflammatory or proliferative disease.

It is therefore an object of the present invention to provide a combination therapy using vitamin B12 compounds with interferon compounds for the enhanced treatment of viral, inflammatory or proliferative diseases.

SUMMARY OF THE INVENTION

The invention comprises a pharmaceutical composition for the treatment of a disease selected from the group consisting of viral diseases; proliferative diseases; inflammatory diseases; proliferative and inflammatory diseases; proliferative and viral diseases; viral and inflammatory diseases; and proliferative, viral and inflammatory diseases; comprising: (1) at least one vitamin B12 compound; and (2) at least one interferon compound.

Another embodiment of this invention comprises a pharmaceutical composition for the treatment of proliferative diseases, such as cancer comprising at least one vitamin B12 compound and at least one interferon compound.

Yet another embodiment of this invention comprises a pharmaceutical composition for the treatment of viral diseases, such as hepatitis B, hepatitis C, herpes, or vesticular stomatitis comprising at least one vitamin B12 compound and at least one interferon compound.

Yet another embodiment of this invention comprises a pharmaceutical composition for the treatment of inflammatory diseases comprising at least one vitamin B12 compound and at least one interferon compound.

Yet another embodiment of this invention comprises a pharmaceutical composition for the treatment of astrocytoma and glioma comprising at least one vitamin B12 compound and at least one interferon compound.

Another embodiment of this invention comprises a pharmaceutical composition for the treatment of multiple sclerosis comprising at least one vitamin B12 compound and at least one interferon compound, such as interferon-alpha or interferon-beta.

Another aspect of this invention is a pharmaceutical composition for the treatment of hepatitis B comprising vitamin B12 and interferon-alpha or interferon-beta.

Another aspect of this invention is a pharmaceutical composition for the treatment of hepatitis C comprising vitamin B12 and interferon-alpha or interferon-beta.

Another aspect of this invention is a pharmaceutical composition according to any of the aspects outlined above wherein the vitamin B12 compound is conjugated to the second compound.

Another aspect of this invention is a method of treating a viral, proliferative or inflammatory disease, including MS, hepatitis B and hepatitis C, comprising the step of administering to a patient any of the pharmaceutical compositions outlined above.

An other aspect of this invention is a method of treating a viral, proliferative, or inflammatory disease, including MS, hepatitis B and hepatitis C, comprising the steps of administering the vitamin B12 compound at a frequency selected from the group consisting of: more than once daily, daily, more than once weekly, weekly, more than once monthly and monthly, and administering the second compound at a frequency selected from the group consisting of: more than once daily, daily, more than once weekly, weekly, more than once monthly, and monthly.

An other aspect of this invention is a method of treating a viral, proliferative, or inflammatory disease, including MS, hepatitis B and hepatitis C, comprising the steps of administering to a patient, either together or separately, one or more vitamin B12 compound, and one or more interferon compound.

Encompassed within this invention are any of the above treatments wherein the dose of vitamin B12 compound is between 10 and 2500 mg, and/or the dose of interferon compound is similar or less than the interferon therapeutic dose range used.

Another aspect of this invention is the use of any of the compounds described above to treat a viral, proliferative, or inflammatory disease.

Definitions

Prior to setting forth the invention, it may be helpful to an understanding thereof to first set forth definitions of certain terms that will be used hereinafter.

"CFA" means complete Freunds' adjuvant.

"DM20" means an isoprotein proteolipid protein. It is a major integral membrane protein of the central nervous system (CNS). DM20 is normally expressed in early (postnatal) stages of growth.

"EAE" or "experimental autoimmune encephalomyelitis" means a mouse model; the immunosuppressive mouse model for multiple sclerosis.

"Enhanced", "enhancing" or "enhances", used in the context of, for example, "enhanced effectiveness", means an enhanced therapeutic effect, and includes a synergistic effect.

"Inflammatory diseases" means a class of diverse diseases and disorders that are characterized by any one of the following: the triggering of an inflammatory response; an upregulation of any member of the inflammatory cascade; the downregulation of any member of the inflammatory cascade. Inflammatory diseases include diabetes, artheriosclerosis, inflammatory aortic aneurysms, restenosis, ischemia/reperfusion injury, glomerulonephritis, sacoidosis cancer, restenosis, reperfusion injury, rheumatic fever, systemic lupus erythematosus, rheumatoid arthritis, Reiter's syndrome, psoriatic arthritis, ankylosing spondylitis, coxarthritis, inflammatory bowel disease, ulcerative colitis, Crohn's disease, pelvic inflammatory disease, multiple sclerosis, diabetes, osteomyelitis, adhesive capsulitis, oligoarthritis, osteoarthritis, periarthritis, polyarthritis, psoriasis, Still's disease, synovitis, Alzheimer's disease, Parkinson's disease, amyotrophic lateral sclerosis, osteoporosis, inflammatory dermatosis and wound healing. The singular term "inflammatory disease" includes any one or more diseases or disorders selected from the class of inflammatory diseases, and includes any compound or complex disease state wherein a component of the disease state includes a disease or disorder selected from the class of inflammatory diseases.

"Interferon compounds" means interferon-alpha, interferon-alpha analogues, interferon-alpha derivatives, interferon-alpha conjugates, interferon beta, interferon-beta analogues, interferon-beta derivatives, interferon-beta conjugates and mixtures thereof. Interferon-alpha and interferon-beta genes may be altered by, for example, oligonucleotide directed mutagenesis to produce interferon-beta analogues thereof, such as the human recombinant cysteine depleted or cysteine replaced analogues. Further, identity or location of more than one amino acid may be changed by targeted mutagenesis. The primary amino acid sequence of the protein may be augmented by glycosylation or by other supplementary molecules such as lipids, phosphate, and acetyl groups. Further, individual amino acids residues in the chain may be modified by oxidation, reduction, or other derivatization. The interferon-alpha or interferon-beta protein may be cleaved to obtain the fragments which retain activity. The whole protein or its fragments can be fused with other peptides and proteins such as immunoglobulins and other cytokines. Interferon-alpha and interferon-beta conjugates may represent, for example, a composition comprising interferon-beta coupled to a non-naturally occurring polymer comprising a polyalkylene glycol moiety. Preferred interferon compounds include Roferon®, Intron®, Alferon®, Infergen®, Omniferon®, Alfacon-1, interferon-alpha, interferon-alpha analogues, pegylated interferon-alpha, polymerized interferon-alpha, dimerized interferon-alpha, interferon-alpha conjugated to carriers, interferon-alpha as oral inhalant, interferon-alpha as injectable compositions, interferon-alpha as a topical composition, Roferon® analogues, Intron® analogues, Alferon® analogues, and Infergen® analogues, Omniferon® analogues, Alfacon-1 analogues, interferon beta, Avonex™, Betaseron™, Betaferon™, Rebif™, interferon-beta analogues, pegylated interferon-beta, polymerized interferon-beta, dimerized interferon-beta, interferon-beta conjugated to carriers, interferon-beta as oral inhalant, interferon-beta as an injectable composition, interferon-beta as a topical composition, Avonex™ analogues, Betaseron™, Betaferon™ analogues, and Rebif™ analogues. Alternatively, agents that induce interferon-alpha or interferon-beta production or mimic the action of interferon-alpha or interferon-beta may also be employed. The singular form, "interferon compound", may mean any one or more compounds from the class of interferon compounds.

"MBP" means myelin basic protein.

"Mimetic peptide" means a peptide that biologically mimics active determinants on hormones, cytokines, enzyme substrates, viruses or other bio-molecules, and may stimulate, antagonize or otherwise modulate the physiological activity of natural ligands.

"ND4 mouse model" means a transgenic mouse model for multiple sclerosis, produced by transformation with multiple copies of DM20; the genetic mouse model for multiple sclerosis.

"PBS" or "phosphate buffer saline" means an injectable solution that serves as a negative control because it does not have any physiological or therapeutic effects.

"PLP" means an isoprotein proteolipid protein. PLP becomes predominant in the adult.

"Proliferative diseases" means a class of diverse diseases and disorders characterized by a lack of control or poorly controlled cell division or proliferation. Proliferative diseases include anal cancer, bile duct cancer, colon cancer, esophageal cancer, gallbladder cancer, pancreatic cancer, small intestine cancer, stomach cancer, osteosarcoma, ovarian epithelial cancer, gestational trophoblastic tumor, uterine sarcoma, vaginal cancer, vulvar cancer, ovarian germ cell tumor, soft tissue sarcoma, acute lymphoblastic leukemia, acute myeloid leukemia, small cell lung cancer, malignant mesothelioma, malignant thymoma, hypopharyngeal cancer, laryngeal cancer, nasopharyngeal cancer, oropharyngeal cancer, parathyroid cancer, salivary gland cancer, brain tumor, glioma, cerebellar astrocytoma, cerebral astrocytoma, ependymoma, medulloblastoma, adrenocortical carcinoma, pituitary tumor, islet cell carcinoma, bladder cancer, kidney cancer, penile cancer, Wilm's tumor, AIDS-related lymphoma, cutaneous T-cell lymphoma, hodgkin's lymphoma, Ewing's sarcoma, chronic myelogenous leukemia, hemangiomas of infancy and childhood, mycosis funoides, hairy cell leukemia, Kaposi's sarcoma, non-hodgkin's lymphoma, multiple myeloma, basal cell carcinoma, malignant melanoma, colorectal cancer, non-small cell lung carcinoma, bladder cancer, pancreatic carcinoma, renal cell carcinoma, neuroblastoma, bladder cancer, breast cancer, cervical cancer, liver cancer, sarcomas, thyroid cancer, endometrial cancer, uterine cancer, multiple myeloma, testicular cancer, retinoblastoma, colorectal cancer, oral cancer, rectal cancer, prostate cancer, restenosis, arteriosclerosis, proliferative diabetic retinopathy. The singular form "proliferative disease" includes any one or more diseases selected from the class of proliferative diseases, and includes any compound or complex disease state wherein a component of the disease state includes a disease selected from the class of proliferative diseases.

"PTX" or "pertussis toxin" means the major protein toxin produced by virulent strains of Bordetella pertussis, the organism that causes whooping cough. PTX is a potent ancillary adjuvant that primes macrophages used to elicit several different autoimmune diseases, including EAE.

"SJL/J" means a mouse model. Specifically, a Female SJL/J mouse has increased susceptibility to development of autoimmune disease. A SJL/J transgenic mouse strain is susceptible to induction of EAE (more susceptible to development of EAE than most other mouse strains). Tumor development as well as autoimmunity in this mouse may result from an effective amplification of the immune response.

"Synergistic" means a greater anti-inflammatory, anti-proliferative and/or anti-viral effect with the use of a combination therapy of vitamin B12 and anti-inflammatory, anti-proliferative, and/or anti-viral compounds than with the use of any of these therapeutic compounds alone. This synergistic effect can work through either similar or different mechanisms or pathways of action. One advantage of a combination therapy with a synergistic effect is that standard dosages can be used for a greater therapeutic effect than expected from the addition of the effect of either compound administered alone; or alternatively lower dosages or reduced frequency of administration of the therapeutic compound(s) may be used to achieve a better therapeutic effect.

"Viral diseases" means a class of diverse diseases and disorders caused by or believed to be caused by viruses. The class of viral diseases includes genital warts (HPV), HIV/AIDS, herpes, influenza, measles, polio, varicella-zoster, hepatitis A, hepatitis B, hepatitis C, hepatitis D, hepatitis E, hepatitis G., meningitis, genital warts (HPV), vesticular stomatitis virus infection, and dengue fever. The singular form "viral disease" includes any one or more diseases selected from the class of viral diseases, and includes any compound or complex disease state wherein a component of the disease state includes a disease selected from the class of viral diseases.

"Vitamin B12 compounds" means a class of compounds which includes vitamin B12 and its analogues, derivatives or conjugates. The class of vitamin B12 compounds includes cyanocobalamin (CN-Cbl), aquacobalamin, adenosylcobalamin, methylcobalamin, hydroxycobalamin (HC), cyanocobalamin carbanalide, and 5-o-methylbenzylcobalmin [(5-OmeB-za)CN-Cbl] as well as the desdimethyl, monoethylamide and the methylamide analogues of all of the above. Also included are the various analogues and homologues of cobamamide such as coenzyme B12 and 5-deoxydenosylcobalamin. Other analogues include chlorocobalamin, sulfitocobalamin, nitrocobalamin, thiocyanatocobalamin, benzimidazole derivatives such as 5,6-dichlorobenzimidazole, 5-hydroxybenzimidazole, trimethylbenzimidazole, as well as adenosylcyanocobalamin [(Ade) CN-Cbl], cobalamin lactone, cobalamin lactam and the anilide, ethylamide, monocarboxylic and dicarboxylic acid derivatives of vitamin B12 or its analogues. Preferred derivatives of vitamin B12 include the mono-, di- and tricarboxylic acid derivatives or the proprionamide derivatives of vitamin B12. In addition, the compositions include polymers of these analogues or vitamin B12 conjugated to other molecules or encapsulated. The singular form, "vitamin B12 compound", means any one or more compounds from the class of vitamin B12 compounds.

DETAILED DESCRIPTION OF THE INVENTION

The current invention discloses the effect of vitamin B12 compounds alone and in combination with interferon compounds for treatment of viral, inflammatory or proliferative diseases. Vitamin B12 compounds alone show efficacy and clearly show an enhancing or synergistic effect in combination with interferon compounds for treating viral, inflammatory, and proliferative diseases.

Pharmaceutical Composition

The present invention provides pharmaceutical compositions for enhancing anti-viral, anti-proliferative and anti-inflammatory effects and pharmaceutical compositions for treatment of viral, proliferative and inflammatory diseases. The pharmaceutical composition comprises a first compound that is a vitamin B12 compound and a second compound that is an interferon compound.

Excipients

The pharmaceutical compositions of the invention preferably contain a pharmaceutically acceptable carrier or excipient suitable for rendering the compound or mixture administrable orally, intranasally, or parenterally, intravenously, intradermally, intramuscularly or subcutaneously, rectally, via inhalation or via buccal administration, or transdermally. The active ingredients may be admixed or compounded with any conventional, pharmaceutically acceptable carrier or excipient. It will be understood by those skilled in the art that any mode of administration, vehicle or carrier conventionally employed and which is inert with respect to the active agents may be utilized for preparing and administering the pharmaceutical compositions of the present invention. Illustrative of such methods, vehicles and carriers are those described, for example, in *Remington's Pharmaceutical Sciences*, 4th ed. (1970). Those skilled in the art, having been exposed to the principles of the invention, will experience no difficulty in determining suitable and appropriate vehicles, excipients and carriers or in compounding the active ingredients therewith to form the pharmaceutical compositions of the invention.

The compositions of the invention may also be conjugated to transport molecules, monoclonal antibodies or transport modalities such as vesicles and micelles that preferentially target recipient cells.

Administration

The compounds of the present invention in the described dosages are administered orally, intranasally, by inhalation, intraperitoneally, subcutaneously, intramuscularly, transdermally, sublingually or intravenously. For oral administration the pharmaceutical composition can be prepared, for example, in the form of tablets, troches, capsules, elixirs, suspensions, syrups, wafers, chewing gum or the like prepared by procedures known to those skilled in the art. The amount of active compound in such therapeutically useful compositions or preparations is such that a suitable dosage will be obtained.

The therapeutically effective amount of compound to be included in the pharmaceutical composition of the invention depends, in each case, upon several factors, e.g., the type, size and condition of the patient to be treated, the intended mode of administration, the capacity of the patient to incorporate the intended dosage form, the severity of the disease progression, etc.

The dosages used for each interferon compound are similar to those dosages known to those skilled in the art and used in pre-clinical and clinical studies and in commercial use. The concentrations may be lower than the currently used dosages as the combination of these compounds with vitamin B12 increases efficacy of these compounds. Indeed, vitamin B12 may be combined with interferon compounds with the objective to reduce the dosages of the interferon compounds, in order to achieve both effective treatment and to lessen the negative effects of the interferon compounds.

The dosages for interferon-alpha and interferon-beta are known in the art. For example, doses for interferon-beta typically range from 30 $\mu$g to 250 $\mu$g. The main differences between Avonex™, Betaseron™ and Rebif™ are the amount of interferon-beta given and the route and frequency of administration. Avonex™ is preferably administered in the amount of 30 $\mu$g by intramuscular injection once weekly; Betaseron™ is preferably administered in the amount of 250 $\mu$g by subcutaneous injection every other day; and Rebif™ is preferably administered in the amount of 44 $\mu$g by subcutaneous injection three times a week. Several clinical studies have used a dose of up to 9 MIU every other day or thrice weekly of recombinant interferon alpha-2a in treatment of multiple sclerosis (Durelli et al, 1996, Nyland et al, 1996). The dosage generally used for both non-pegylated and pegylated interferon-alpha-2a or 2b for clinical indications for hepatitis C range from 3MIU–10 MIU three times a week for non-pegylated form and ~70 $\mu$g to 180 $\mu$g weekly (Komanduri and Cotler, 2002). Interferon dosage used in the treatment of proliferative diseases such as hairy cell leukemia range from 1–36 MIU, daily or twice weekly.

The preferred dosage of a vitamin B12 compound for the present invention is the maximum a patient requires to provide an optimal enhancing effect, such maximum being tempered by the absolute upper limit of vitamin B12 compound dosage being the maximum that a patient can tolerate and not develop any serious complications. Vitamin B12 compounds have been available for many years as an injectable treatment for pernicious anemia, with doses typically in the range of 1000 $\mu$cg. Vitamin B12 compounds also have a long history as a general oral health supplement with doses also in the "$\mu$cg" range. Hydroxocobalamin, a vitamin B12 compound, is available as a cyanide poisoning antidote, called Cyanokit® (U.S. Pat. No. 5,834,448). Cyanokit® is an acute one-time 5-gram dose of hydroxocobalamin administered for emergency purposes. Though vitamin B12 has been proposed for use for the therapeutic treatment for a few inflammatory diseases, no person has demonstrated that high doses of B12 in combination with an interferon compound would achieve an enhanced therapeutic effect. With our experimental studies, no toxicity has been found in animals, even at concentrations of 15 mg/kg of vitamin B12 in mice. In a previous acute toxicity study, no toxicities were observed in mice and rabbits at doses of vitamin B12 (hydroxocobalamin) up to 1 g/kg and 100 mg/kg body weight, respectively (Mizoule, 1966). The dosage of vitamin B12 compound for our invention are within the range of 10 mg to 2.5 g daily.

Those skilled in the art will be aware that the amounts of the various components of the compositions of the invention to be administered in accordance with the invention to a patient will depend upon those factors noted above.

Methods and Uses

The present invention provides methods to enhance or potentiate interferon compound-induced anti-viral, antiproliferative and anti-inflammatory effects and methods of treating viral, proliferative or inflammatory diseases in patients by administering an amount of vitamin B12 compound in combination with an interferon compound. Vitamin B12 compounds can be administered simultaneously, separately or in combination with interferon compounds, under different dose and route regimens, to enhance the efficacy of interferon compounds in the treatment of viral, proliferative or inflammatory diseases in patients compared to when such compounds are administered alone.

The first method of treatment is the administration of a pharmaceutical composition including both a vitamin B12 compound and an interferon compound. An alternate method of treatment includes the step of the administration of a pharmaceutical composition including a vitamin B12 compound followed by the step of the administration of a second pharmaceutical composition including an interferon compound. Optionally, the administration of the vitamin B12 compound can follow the administration of the interferon compound. Optionally, the administration of the pharmaceutical compositions can occur separately or simultaneously.

The following are examples of acceptable regimens:

1. More than once daily, daily, more than once weekly, weekly, more than once monthly or monthly mixtures of vitamin B12 compound in combination with interferon compounds for the effective treatment of anti-viral, antiproliferative and anti-inflammatory diseases;

2. More than once daily, daily, more than once weekly, weekly, more than once monthly or monthly mixtures of vitamin B12 compound simultaneously with interferon compounds for the effective treatment of anti-viral, antiproliferative and anti-inflammatory diseases;

3. More than once daily, daily, more than once weekly, weekly, more than once monthly or monthly treatments with interferon compounds and vitamin B12 compounds administered separately either more than once daily, daily, more than once weekly, weekly, more than once monthly, or monthly;
4. More than once daily, daily, more than once weekly, weekly, more than once monthly or monthly mixtures of interferon compounds and vitamin B12 compounds, as well as adjunct administration of more than once daily, daily, more than once weekly, weekly, more than once monthly or monthly doses of vitamin B12 compounds.

Those skilled in the art will readily understand that the pathologies and disease states expressly stated herein are not intended to be limiting. Rather the compounds of the present invention may be used to treat any disease that features an inflammatory, proliferative or viral response.

EXAMPLES

The examples below are exemplary of the embodiments of the present invention.

(A) Examples Demonstrating Anti-Inflammatory Effects of Interferon-Based Combination Therapies With Vitamin B12 Compounds

Example 1

Effect of Vitamin B12, Interferon-Beta and Combination of Vitamin B12 Incorporating Interferon-Beta in ND4 Mouse Model Rationale:

Vitamin B12 and interferon-beta were used in a demyelinating transgenic mouse model to demonstrate a synergistic effect when a combination of vitamin B12 and interferon were used in the treatment of such diseases as compared to treatment with interferon or vitamin B12 alone.

Experimental Protocol:

The ND4 model was used as a slow progressive demyelinating transgenic mouse model where the animals demonstrate symptoms in young adults at approximately 3 months of age. The severity of the clinical signs increased until a maximum around 6 months with animals dying around 8 to 9 months of age. Clinical signs assessed included general shaking, seizures, head jerk, hind limb and tail shiver, wobbly gait and limp tail. The scale of zero (absence) to four (constant and uncontrollable movements) was used for each of the clinical signs.

Mice (4 animals per group) were treated with vitamin B12 (cyanocobalamin) alone at a dose of 15 mg/kg; weekly and in combination with interferon-beta 1a (Rebif™). Interferon-beta 1a was administered alone and in combination with vitamin B12 at a dose of interferon-beta 1a at a dose of 5000 IU, tri-weekly. All treatments began when the mice reached 3 months of age at which time signs of demyelinating disease were evident. Treatment was stopped at time of sacrifice.

Figure 1:
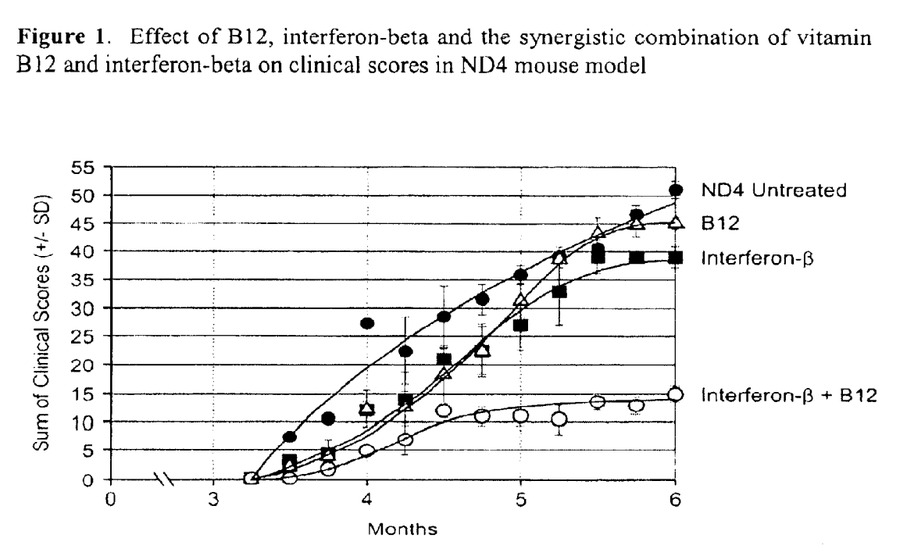
FIG. 1 is a graph showing the effect of vitamin B12, interferon-beta and the combination of vitamin B12 and interferon-beta on clinical scores in the ND4 mouse model.

Results and Conclusions:

Treatment of the ND4 mice with interferon-beta or vitamin B12 showed attenuation of clinical signs of MS, an inflammatory disease (FIG. 1) but the combination therapy of interferon-beta and vitamin B12 had a synergistic effect in reducing the clinical signs of the inflammatory disease than interferon-beta or vitamin B12 alone.

Example 2

Effect of Vitamin B12, Interferon-Beta and Combination of Vitamin B12 With Interferon-Beta in EAE Mouse Model Rationale:

Vitamin B12 and interferon-beta were used in an autoimmune EAE model to demonstrate an enhancing effect when a combination of vitamin B12 and interferon were used in the treatment of such diseases as compared to treatment with either interferon or vitamin B12 alone.

Experimental Protocol:

Experimental Allergic Encephalomyelitis (EAE) was induced in 7–8 week old female SJL mice. Each mouse was injected intravenously with 200 ng Pertussis Toxin (PT) in 100 1 total volume at a tail vein on day 1. Following 48 hours, 200 ng PT was injected a second time. Tail vein injections were done with 30.5 gauge needles. Following the PT injection was a one time MBP/CFA (Becton Dickinson) emulsion injection. Each mouse was injected subcutaneously using a 27.5 gauge needle with 200 µg/50 1 of MBP emulsified in 50ul of complete Freund's adjuvant (CFA) at the base of the tail. The total injection volume was 100 µl. The mice were observed daily after first injection and the clinical signs of disease were recorded. These included unsteady gait, shaking, tail drop, weight loss, etc. Clinical scores were evaluated every other day starting on day 7 following immunization. Animals were treated daily for 11 days.

Mice (4 animals per group) were treated with vitamin B12 (cyanocobalamin) alone at a dose of 10 mg/kg; daily and in combination with interferon-beta. Interferon-beta 1a (Rebif™) was administered alone and in combination with vitamin B12 at a dose of 5000 IU, daily; Vitamin B12 and interferon-beta were administered as separate injections starting on the day of first immunization. Treatment was stopped at time of sacrifice. Mice were monitored daily from day 7 after immunization for clinical signs of EAE and were scored on a scale of 0 to 5. A score of 0 represented the absence of signs while a score of 5 was given to moribund animals.

Figure 2:
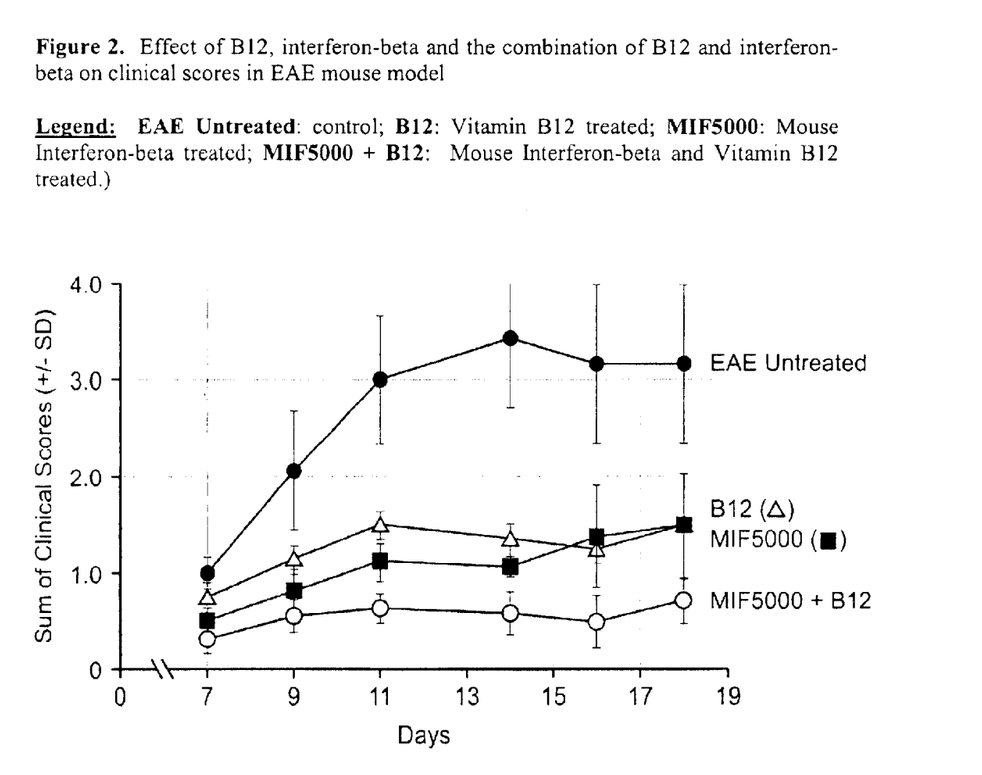
FIG. 2 is a graph showing the effect of vitamin B12, interferon-beta and the combination of vitamin B12 and interferon-beta on clinical scores in the EAE mouse model.

Results and Conclusions:

Treatment of the EAE mice with interferon-beta alone showed attenuation of clinical signs of the inflammatory disease (FIG. 2) but the combination therapy of interferon-beta and vitamin B12 was more effective in reducing the clinical signs of the inflammatory disease, indicating the combination of interferon-beta and vitamin B12 were effective in enhancing the anti-inflammatory activity of interferon-beta.

Example 3

Effect of Interferon Concentration on B12 Synergistic Effects

Rationale:

Vitamin B12 (cyanocobalamin) and varying concentrations of interferon-beta were used in the ND4 transgenic model described above to demonstrate concentration effect of interferon on B12 synergistic effects.

Experimental Protocol:

ND4 mice were either (a) untreated or treated with (b) interferon-beta 1a (Rebif™) alone (5000 IU) or (c) 1000 IU of interferon-beta 1a and B12 (15 mg/kg), or (d) 2500 units of interferon-beta 1a and B12 (15 mg/kg) or (e) 5000 IU of interferon-beta 1a and B12 (15 mg/kg) three times a week for the duration of the experiment. Treatment was started when the animals were 3 months of age and continued for 11 weeks. The animals were evaluated twice a week for clinical signs and the scores were averaged on a weekly basis. Refer to example 1 for more experimental details.

Results and Conclusions:

The results demonstrated that the effectiveness of the combination therapy was dependent on the concentration of interferon-beta, with significant reduction of clinical scores (at interferon-beta concentration of 5000 IU). Thus, by combining vitamin B12 and interferon-beta, a lower levels of interferon needed was needed to achieve pharmacological action. (Table 1).

TABLE 1

Effect of interferon-beta concentration on vitamin B12 synergistic effect on the clinical signs and symptoms in the transgenic mouse at six months

| Treatment | Sum of Clinical Scores (+/− SD) |
| --- | --- |
| ND4 Untreated | 22 +/− 2 |
| interferon-beta (5000 IU) | 21 +/− 4 |
| interferon-beta (1000 IU) + Vitamin B12 (15 mg/kg) | 18 +/− 1 |
| interferon-beta (2500 IU) + Vitamin B12 (15 mg/kg) | 16 +/− 1 |
| interferon-beta (5000 IU) + Vitamin B12 (15 mg/kg) | 13 +/− 2 |

(B) Examples Demonstrating Anti-Proliferative Effects of Interferon-Based Combination Therapies Incorporating Vitamin B12 Compounds

Example 4

Effect of Vitamin B12, Interferon and Combination of Vitamin B12 With Interferon in Inhibiting Cellular Proliferation In Vitro Rationale:

Interferon was a therapeutic agent that has been reported to be effective in treating proliferative diseases such as Kaposi's sarcoma, melanoma, fibrosarcoma and high-grade astrocytoma (Fine et al., 1997). The following experiment was carried out to determine whether vitamin B12 could enhance the anti-proliferative effects of interferon in astrocytoma cell lines.

Experimental Protocol:

Mouse ascite astrocytoma cells were seeded in a 96-well plate and grown to 60% confluence in standard growth conditions. Prior to treatment, cells were washed and the culture medium was replaced with culture medium containing (a) interferon-beta alone (500 IU/ml), (b) vitamin B12 (methylcobalamin)(25 μg/ml) alone, or (c) a combination of interferon-beta (500 IU/ml), and vitamin B12 (25 μg/ml), and incubated overnight.

The CellTiter 96® AQ$_{ueous}$ One Solution Cell Proliferation Assay was used as a colorimetric method for determining the number of viable cells in proliferations. Cell proliferation assays were performed by adding a small amount of the CellTiter 96® AQ$_{ueous}$ One Solution Reagent directly to culture wells, incubating for 1–4 hours and then recording absorbance at 490 nm with a 96 well plate reader. The quantity of formazan product as measured by the amount of 490 nm absorbance is known in the art to be directly proportional to the number of living cells in the culture.

Results and Conclusions:

Treatment of either mouse interferon-beta or vitamin B12 (methylcobalamin) alone resulted in a decrease in proliferative activity as compared to untreated cells. However, antiproliferative activity was significantly increased when cells were treated with a combination of vitamin B12 and interferon-beta (Table 2 below) as compared to treatment with either vitamin B12 or interferon-beta alone.

TABLE 2

Effect of combination therapy on cellular proliferation in a mouse astrocytoma cell line

| Treatment | Measure of Proliferative Activity (Absorbance at 490 nm) |
| --- | --- |
| No treatment | 0.8955 |
| Treatment with Mouse Interferon-beta (500 IU/ml) | 0.3855 |
| Treatment with Vitamin B12 (25 μg/ml) | 0.2985 |
| Treatment with Mouse Interferon-beta (500 IU/ml) and Vitamin B12 (25 μg/ml) | 0.1435 |

Example 5

Effect of Vitamin B12, Interferon, Combination of Vitamin B12 With Interferon on Astrocyte Gliosis Rationale:

Astrocyte gliosis refers to the increased reactivity and proliferation of astrocytes in the central nervous system and is thought to play a major role in the development of lesions in the brain. Specifically, astrocyte gliosis has been observed around hematogenous metastases of the human brain and GFAP, the protein marker for reactive astrocytes, has been used as a biomedical marker for early detection for chemically induced cancer. Both the ND4 and EAE mouse models were used below to illustrate the effect of the combination therapy on astrocyte gliosis. The ND4 transgenic mice develops normally up to three months, after which demyelination progresses thereafter. Along with primary demyelination, astrogliosis increases from about twice normal levels at three months to extensive astrogliosis by adult stage. Similarly, the EAE-induced mice had also been shown to demonstrate extensive astrogliosis.

(a) ND4 Model

Experimental Protocol:

ND4 mice were treated as described previously in Example 1. After the various treatments, the mice were sacrificed and brain sections removed for GFAP staining and quantitation. The brain region of hippocampus, adjacent to the dentate gyrus was fixed in formalin, paraffin-embedded and sectioned at 5 μm. Immunohistochemistry with anti-GFAP antibody was used to stain for GFAP. Glial fibrillary acidic protein was a protein expressed by astrocytes (particularly reactive astrocytes) and is used as a marker for these cells.

In addition, quantification of GFAP within the brains of normal, ND4 untreated and ND4 treated mice was carried out to provide a more precise level of protein expression. Whole brain homogenates were assayed for GFAP by slot blot. Brains were homogenized in a buffer containing 50 mM Tris-HCl pH 7.6, 0.5 mM DTT, 1 mM EDTA, and 0.43 mM PMSF. The homogenate was centrifuged at 11000 rpm for 30 min at 4° C. The pellet was isolated and resuspended in a buffer containing 10 mM sodium phosphate pH 7.5, 2 mM DTT, 6 M urea and 1 mM EDTA. Samples were loaded onto the slot blot apparatus (BioDot, Biorad) under vacuum. The blots were reacted with anti-GFAP antibodies and then a secondary antibody. The blots were developed and the relative amounts of each band quantified.

Figure 3:
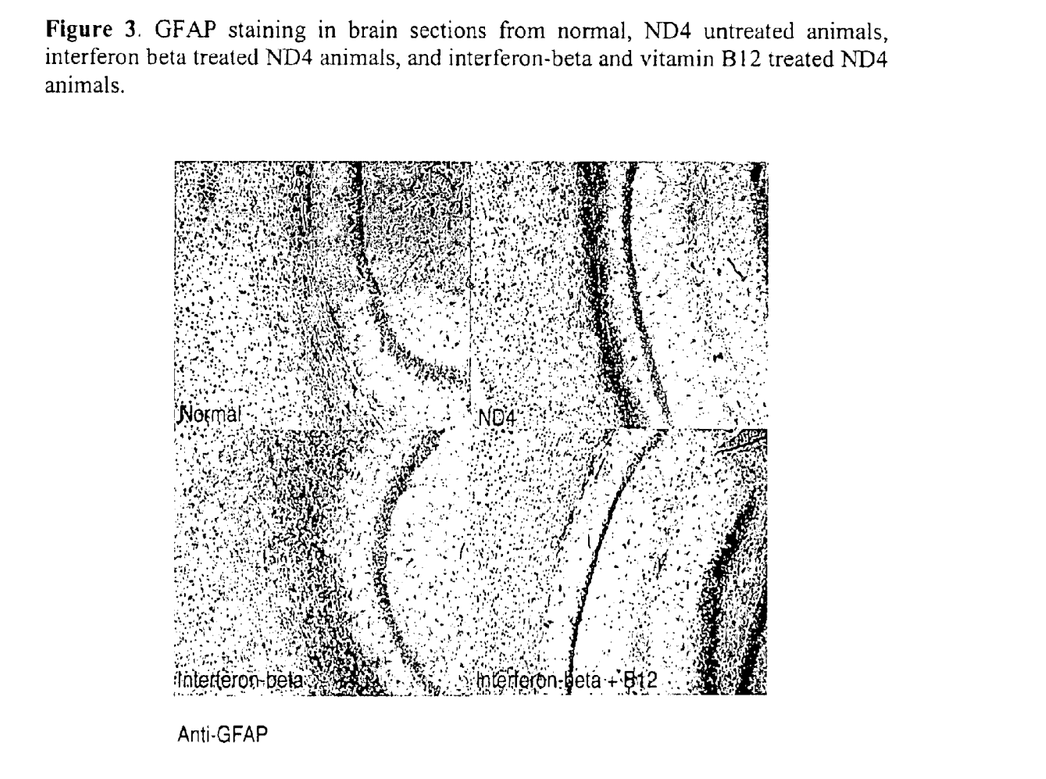
FIG. 3 is a graph showing the GFAP staining in brain sections from normal, ND4-untreated animals, interferon-beta treated ND4 animals, and interferon-beta/vitamin B12 treated ND4 animals.

Results and Conclusions:

There was a significant increase in GFAP staining of untreated ND4 animals compared to normal animals (FIG. 3), indicating extensive astrocyte gliosis. This high level of GFAP staining was decreased in interferon-beta treated animals. Treatment with interferon decreased the number of activated fibrous astrocytes slightly and the levels of GFAP in brain homogenates. The treatment of interferon-beta and vitamin B12 inhibited the levels of activated astrocytes and levels of GFAP to near normal levels (Table 3). These data clearly demonstrated that the combination treatment of interferon-beta with vitamin B12 acted in a synergistic manner to inhibit astrocyte proliferation and activation.

TABLE 3

Total relative GFAP in brain homogenates from normal, ND4 untreated animals, vitamin B12-treated, interferon-beta treated; and interferon-beta and vitamin B12 treated ND4 animals.

| Treatment | Relative Amount of GFAP (+/− SD) |
|---|---|
| Normal | 1.0 |
| Untreated ND4 mice | 4.4 +/− 0.2 |
| Vitamin B12 (15 mg/kg) | 2.8 +/− 0.1 |
| interferon-beta (5000 IU/ml) | 3.1 +/− 0.1 |
| interferon-beta (5000 IU/ml) + Vitamin B12 (15 mg/kg) | 1.6 +/− 0.2 |

(b) EAE Model

Experimental Protocol:

EAE mice were treated as described previously in Example 2. After the various treatments, the mice were sacrificed and brain sections removed for GFAP staining and quantitation. The brain region of hippocampus, adjacent to the dentate gyrus was fixed in formalin, paraffin-embedded and sectioned at 5 μm. Immunohistochemistry with anti-GFAP antibody was used to stain for GFAP. Glial fibrillary acidic protein was a protein expressed by astrocytes (particularly reactive astrocytes) and is used as a marker for these cells.

In addition, quantification of GFAP within the brains of normal, EAE untreated and EAE treated mice was carried out to provide a more precise level of protein expression. Whole brain homogenates were assayed for GFAP by slot blot. Brains were homogenized in a buffer containing 50 mM Tris-HCl pH 7.6, 0.5 mM DTT, 1 mM EDTA, and 0.43 mM PMSF. The homogenate was centrifuged at 11000 rpm for 30 min at 4° C. The pellet was isolated and resuspended in a buffer containing 10 mM sodium phosphate pH 7.5, 2 mM DTT, 6 M urea and 1 mM EDTA. Samples were loaded onto the slot blot apparatus (BioDot, Biorad) under vacuum. The blots were reacted with anti-GFAP antibodies and then a secondary antibody. The blots were developed and the relative amounts of each band quantified.

Results and Conclusions:

Treatment with vitamin B12 was not effective in decreasing the levels of GFAP while treatment of interferon-beta was able to reduce the amounts of GFAP by ~50%. However, treatment of interferon-beta and vitamin B12 was the most effective among the treatment groups. The combination therapy inhibited the levels of activated astrocytes and levels of GFAP to near normal levels (Table 4). These data clearly demonstrated that the combination treatment of interferon-beta with vitamin B12 acted in a synergistic manner to inhibit astrocyte proliferation and activation.

TABLE 4

Total relative GFAP in brain homogenates from normal, EAE untreated animals, vitamin B12 treated interferon-beta treated; and interferon-beta and vitamin B12 treated EAE animals.

| Treatment | Relative Amount of GFAP (+/− SD) |
|---|---|
| Normal | 1.0 |
| Untreated EAE mice | 4.2 +/− 0.2 |
| Vitamin B12 (15 mg/kg) | 4.2 +/− 0.2 |
| interferon-beta (5000 IU/ml) | 2.0 +/− 0.5 |
| interferon-beta (5000 IU/ml) + Vitamin B12 (15 mg/kg) | 1.4 +/− 0.2 |

(C) Examples Demonstrating Anti-Viral Effects of Interferon-Based Combination Therapies With Vitamin B12

Example 6

In Vitro Studies Demonstrating The Enhancing Effect of Interferon Compound With Vitamin B12 Compounds on Treatment of Human Hepatitis B Virus (HBV)

Rationale:

Hep G2.2.15 was a HepG2 cell line that was stably transfected with HBV genome and that continues to secrete HBV virions into the cell growth medium. This cell line had been widely used to study the activities of anti-viral agents against HBV infection and was used in this study to evaluate the enhancing effect of vitamin B12 compounds with interferon compounds on treating HBV infections. Interferon was used to treat both hepatitis B and C in the clinic.

Experimental Protocol:

HepG2.2.15 cells, a cell line that was stably transfected with HBV genome, were cultured in RPMI-1640 with fetal bovine serum at either 2 or 4% final concentration and with no antibiotics. The cells were seeded in a 96-well plate at a density of $2 \times 10^4$ cells/well and grown overnight. The medium was then discarded and replaced with 100 μl of culture medium containing hydroxocobalamin (a form of vitamin B12) alone (at various concentrations), interferon-beta alone (at various international units), and the mixture of varying doses of hydroxocobalamin (HC) and various doses of interferon-beta vs HC. Triplicate samples were measured for each concentration. The cells were incubated at 37° C. for 9 days. Drug/medium was changed daily. On day 9, the culture media containing released HBV virions were harvested and used to extract HBV DNA.

HBV DNA from drug-treated HepG2.2.15 cell culture media was extracted using QIAamp DNA mini kit—blood and body fluid spin column according to manufacturer's instruction. Briefly, 10 μl of QIAGEN proteinase K was added to 1.5 ml Eppendorf tube. 50 μl cell supernatant and 50 μl AL buffer were added to the tube. The samples were incubated at 56° C. water bath for 3 h. At the end of incubation, 50 μl ethanol was added to the sample. The mixture was transferred to a QIAamp spin column and centrifuged at 14000 rpm for 1 min. The filtrate was discarded. 50 μl Buffer AW1 was then added to the column and centrifuged at 14000 rpm for 1 min. Following washing and recentrifugation, DNA was eluted in 50 μl dH$_2$O.

HBV DNA was detected by real-time PCR using Lightcycler assay. The reaction was performed in 20 μl, comprising the following: 6.4/4.8 μl dH$_2$O, 2 μl 25 mM MgCl$_2$, 1 μl 10 μM sense primer, 1 μl 10 μM antisense primer, 8/1.6 μl LightCycler Probe (fluorescein-labeled, 5 μM), 0.8/1.6 μl LightCycler Probe 2 (LC Red 640-labeled, 10 μM), 2 μl LC FastStart DNA Master Hyb Probes, 1 μl uracil DNA glycosylase.

PCR mix was aliquoted into glass capillaries and 5 1 DNA template was then added to the PCR mix. A range of HBV plasmid DNA ($1\times10^8$, $1\times10^7$, $1\times10^6$, . . . , $1\times10^2$, 25 copies) was used as standards for quantitative analysis. The cycling conditions are shown in Table 4.

TABLE 4

The cycling conditions for Lightcycler assay

| Program | # cycles | Target Temp | Incubation Time | Temp Transition | Acquisition Mode |
|---|---|---|---|---|---|
| Denaturation | 1 | 95° C. | 9 min | 20° C./sec | None |
| PCR | 45 | 95° C. | 5 sec | 20° C./sec | None |
|  |  | 54° C. | 10 sec | 20° C./sec | Single |
|  |  | 72° C. | 17 sec | 20° C./sec | None |
| Melt | 1 | 98° C. | 0 sec | 20° C./sec | None |
|  |  | 45° C. | 15 sec | 20° C./sec | None |
|  |  | 70° C. | 0 sec | 0.2° C./sec | Continuous |
| Cool | 1 | 40° C. | 30 sec | 20° C./sec | None |

The antiviral effects of the test compounds were calculated using DNA copy numbers as an endpoint. Specifically, the antiviral activities were calculated based on the following formula: Antiviral effect=$(C_{control}-C_{test})/C_{control}$ whereby the $C_{control}$ is the HBV DNA copies in the control wells (without drug); the $C_{test}$ is the HBV DNA copies in the test wells with a given concentration of a test compound.

The enhancing or antagonistic effect was analyzed mathematically using the median effect equation (Chou and Talalay, 1984) by computer software CalcuSyn (Biosoft, St Louis). The range of the combination index (CI) is illustrated in Table 5.

TABLE 5

Correlation of combination index obtained and degree of synergism

| <0.1 | Very strong synergism |
| 0.1–0.3 | Strong synergism |
| 0.3–0.7 | Synergism |
| 0.7–0.85 | Moderate synergism |
| 0.9–1.1 | Additive |
| >1.1 | Antagonism |

Results and Conclusions:

TABLE 6

Antiviral effects of test compounds alone and combinations on HBV measured by HBV DNA copies using Lightcycler assay

| | Concentrations (g/ml) | | | | |
|---|---|---|---|---|---|
| | 0 | 1 | 10 | 100 | 500 |
| HC | 0 | 0.001 | 0.001 | 0.001 | 0.112 |

| | Concentrations (IU/ml) | | | | |
|---|---|---|---|---|---|
| | 0 | 50 | 100 | 500 | 1000 |
| interferon-beta | 0 | 0.569 | 0.746 | 0.773 | 0.823 |

| | Concentrations (g/ml)/(IU/ml) | | | | |
|---|---|---|---|---|---|
| | 0 | 1/50 | 10/100 | 100/500 | 500/1000 |
| HC/interferon-beta | 0 | 0.571 | 0.772 | 0.912 | 0.851 |

TABLE 7

CI values for the combinations between hydroxocobalamin (HC) and interferon-beta on HBV

| HC (μg/ml) | interferon-beta (IU/ml) | CI |
|---|---|---|
| 1 | 50 | 1.908 |
| 10 | 100 | 0.258 |
| 100 | 500 | 0.051 |
| 500 | 1000 | 0.572 |

Viral activity was decreased when cells were treated with interferon-beta but not with vitamin B12. The combination therapy of vitamin B12 with interferon-beta was more effective in attenuating viral activity compared to when these compounds were used alone. There was an enhanced effect for the treatment of hepatitis B infection when vitamin B12 and interferon were combined. See Table 6 for more details.

Specifically, strong and moderate potentiating effects were examined for HC on interferon-beta activity against HBV at the concentrations were higher than 10 μg/ml of HC and 100 IU/ml of interferon-beta, respectively. Based on the outcome of the combination index analysis, the anti-viral effects of interferon-beta with vitamin B12 were synergistic. The results are summarized in Table 7 above.

Example 7

In Vitro Studies Demonstrating the Enhancing Effect of Interferon Anti-Viral Activity With Vitamin B12 on Herpes Simplex Virus Type 2 (HSV-2) and Vesticular Stomatitis Virus (VSV)

Rationale:

MRC-5 (human fibroblast cells) was a HSV and VSV susceptible cell line that was used widely to study the activities of anti-viral agents against VSV and HSV infections. This cell line was used in this study to evaluate the enhancing effect of vitamin B12 compound with interferon-beta and interferon beta on treating VSV and HSV infections.

Experimental Protocol:

A CPE (cytopathic effect) inhibition assay was performed. This assay measures the ability of a drug or agent to protect cells from lysis by a virus. Briefly, confluent MRC-5 cells in a 96-well plate were incubated with various concentrations of hydroxocobalamin (HC) alone, interferon-alpha alone, interferon-beta alone, and the mixtures of varying doses of HC and various doses of interferon-alpha or interferon-beta. The test concentrations for HC were 0, 1, 10, 100, 500 and 1000 μg/ml and that of interferon-alpha and interferon-beta were 0, 5, 10, 50, 100, and 500 IU/ml. Triplicate samples were tested for each concentration in a 96-well plate format. The culture medium for MRC-5 cells was recommended by ATCC (Minimum Essential Medium Eagle with 2 mM L-glutamine and Earle's BSS adjusted to contain 1.5 g/L sodium bicarbonate, 0.1 mM non-essential amino acids, and 1.0 mM sodium pyruvate, 10% fetal bovine serum).

After overnight incubation, the cells were infected with either VSV at moi (multiplicity of infection) of 0.5 pfu/cell or HSV-2 at moi of 0.2 pfu/cell at 37° C. for 1 h. Following removal of virus inoculum, the infected cells were washed with PBS and covered with medium containing either no or increasing concentrations of test compounds as above for 2–3 days at 37° C. until the CPE in the control wells was 100%. The cells protected from CPE were measured using neutral red uptake assay. Specifically, culture medium was removed from cells in a 96-well plate by pump. The cells were then washed once with 200 µl of PBS. 100 µl of 0.01% neutral red (in PBS) was subsequently added to each well, and incubated at 37° C. for 30 min. The dye was then removed and the cells were washed twice with 200 µl PBS per well. The dye was extracted by addition of 100 µl of 50% ethanol/1% glacial acetic acid in PBS to each well and incubated at room temperature for 15 min with gentles shaking at 120–150 rpm. The absorbance at 550 nm was read on an ELISA reader.

The antiviral effects were calculated based on the following formula: Antiviral effect=$(OD_{Test}-OD_0)/(OD_{Control}-OD_0)$ whereby $OD_{Test}$ is the optical density measured with a given concentration of the test compound; $OD_0$ is the optical density measured at drug concentration zero; $OD_{Control}$ is the optical density of uninfected cells.

The potentiating effect was analyzed mathematically using the median-effect equation (Chou and Talalay, 1984) by a computer program CalcuSyn (Biosoft, St Louis). Refer to Table 5 for correlation between combination index obtained and degree of synergism Results and Conclusions:

(a) HSV-2 Infection

The combination therapy of vitamin B12 with interferon-alpha or interferon-beta was more effective in the attenuation of viral activity compared to when these compounds were used alone (Table 8). There was an enhanced effect for the treatment of herpes simplex virus infection when vitamin B12 and interferon, an anti-viral agent, were combined. Specifically, strong potentiating effect was observed for HC on interferon-alpha activity against HSV-2 when the concentrations of HC and interferon-alpha were higher than 10 µg/ml and 10 IU/ml respectively. Strong and moderate potentiating effects were observed for HC on interferon-beta activity against HSV-2 at all concentrations tested. Based on the outcome of the combination index analysis, the anti-viral effects of interferon-alpha or interferon-beta with vitamin B12 were synergistic (Table 9).

TABLE 9

CI values for the combinations between HC and interferon-alpha or interferon-beta on HSV-2

| HC (µg/ml) | interferon-alpha (IU/ml) | CI | HC (µg/ml) | interferon-beta (IU/ml) | CI |
|---|---|---|---|---|---|
| 1 | 5 | 2.292 | 1 | 5 | 0.746 |
| 10 | 10 | 0.07 | 10 | 5 | 0.026 |
| 100 | 50 | 0.117 | 100 | 50 | 0.065 |
| 500 | 100 | 0.009 | 500 | 100 | 0.012 |
| 1000 | 500 | <0.01 | 1000 | 500 | 0.013 |

(b) VSV Infection

Anti-viral activity (as reflected by protection of CPE) was significantly increased when cells were treated with the vitamin B12 or interferon-alpha or interferon-beta. The combination therapy of vitamin B12 with interferon-alpha or interferon-beta was more effective in attenuation viral activity compared to when these compounds were used alone. See Table 10. There was an enhanced effect for the treatment of vesticular stomatitis virus infection when vitamin B12 and interferon, an anti-viral agent, were combined. Specifically, strong potentiating effect was observed for HC on interferon-beta activity against HSV at all concentrations tested and on interferon-alpha activity when the concentrations of HC and interferon-alpha were higher than 100 µg/ml and 50 IU/ml respectively. Based on the outcome of the combination index analysis, the anti-viral effects of interferon-alpha or interferon-beta with vitamin B12 were synergistic (Table 11).

TABLE 8

Antiviral effects of test compounds alone and combinations on HSV-2 determined by CPE inhibition assay

| | Concentrations (µg/ml) | | | | | |
|---|---|---|---|---|---|---|
| | 0 | 1 | 10 | 100 | 500 | 1000 |
| HC | 0 | 0.014 | 0.032 | 0.056 | 0.166 | 0.210 |

| | Concentrations (IU/ml) | | | | | |
|---|---|---|---|---|---|---|
| | 0 | 5 | 10 | 50 | 100 | 500 |
| interferon-alpha | 0 | 0.093 | 0.139 | 0.218 | 0.282 | 0.271 |
| interferon-beta | 0 | 0.164 | 0.136 | 0.314 | 0.281 | 0.265 |

| | Concentrations (g/ml)/(IU/ml) | | | | | |
|---|---|---|---|---|---|---|
| | 0 | 1/5 | 10/10 | 100/50 | 500/100 | 1000/500 |
| HC/interferon-alpha | 0 | 0.090 | 0.257 | 0.342 | 0.724 | 0.999 |
| HC/interferon-beta | 0 | 0.169 | 0.315 | 0.368 | 0.683 | 0.748 |

TABLE 10

Antiviral effects of test compounds alone and combinations on VSV determined by CPE inhibition assay

| | Concentrations ($\mu$g/ml) | | | | | |
|---|---|---|---|---|---|---|
| | 0 | 1 | 10 | 100 | 500 | 1000 |
| HC | 0 | 0.001 | 0.001 | 0.039 | 0.001 | 0.002 |

| | Concentrations (IU/ml) | | | | | |
|---|---|---|---|---|---|---|
| | 0 | 5 | 10 | 50 | 100 | 500 |
| interferon-alpha | 0 | 0.296 | 0.387 | 0.950 | 0.996 | 0.942 |
| interferon-beta | 0 | 0.826 | 0.985 | 0.758 | 0.768 | 0.956 |

| | Concentrations (g/ml)/(IU/ml) | | | | | |
|---|---|---|---|---|---|---|
| | 0 | 1/5 | 10/10 | 100/50 | 500/100 | 1000/500 |
| HC/interferon-alpha | 0 | 0.299 | 0.450 | 0.999 | 0.999 | 0.999 |
| HC/interferon-beta | 0 | 0.999 | 0.999 | 0.999 | 0.999 | 0.999 |

TABLE 11

CI values for the combinations between HC and interferon-alpha or interferon-beta on VSV

| HC ($\mu$g/ml) | interferon-alpha (IU/ml) | CI | HC ($\mu$g/ml) | interferon-beta (IU/ml) | CI |
|---|---|---|---|---|---|
| 1 | 5 | 1.6 | 1 | 5 | 0 |
| 10 | 10 | 1.766 | 10 | 5 | 0 |
| 100 | 50 | 0.013 | 100 | 50 | 0.002 |
| 500 | 100 | 0.027 | 500 | 100 | 0.004 |
| 1000 | 500 | 0.016 | 1000 | 500 | 0.021 |

Summary of Examples

In summary, these examples clearly demonstrate that the combination treatment of a vitamin B12 compound in conjunction with an interferon compound is effective in treating inflammatory, proliferative and/or viral diseases and that B12 enhances the effectiveness of interferon against the disease indicated.

Although the invention has been described with preferred embodiments, it is to be understood that modifications may be resorted to as will be apparent to those skilled in the art. Such modifications and variations are to be considered within the purview and scope of the present invention.

References

Amit B, Oliveira E, Anderson D and Hafler D. Molecular pathogenesis of multiple sclerosis. (1999). Journal of Neuroimmunology 100: 252–259.

Brod S A, Lindsey J W and Wolinsky J S. Combination therapy will glatiramer acetate (copolymer-1 and a type I interferon (interferon-alpha) does not improve experimental autoimmune encephalomyelitis. (2000). Annals of Neurology 47(1): 127–131

Chou T C and Talalay P. Quanatitative analysis of dose-effect relationships: the combined effects of multiple drugs or enzyme inhibitors. (1984). Advances in Enzyme Regulation 22:27–55

Deisenhammer F, Reindl M, Harvey J, Gasse T, Dilitz E and Berger T. Bioavailability of interferon-beta-1b in MS patients with and without neutralizing antibodies. (1999). Neurology 52(6):1239–43

Durelli L, Bongioanni M R, Ferrero B, Imperiale D, Verdun E, Oggero A, Gentile E, Bradac G B , Bergui M, Bergamini L and Bergamasco B. Long term recombinant interferon alpha treatment in MS with special emphasis to side effects. (1996) Multiple Sclerosis 1(6):366–71

Fine H A, Wen P Y, Robertson M, O'Neill A, Kowal J, Loeffler J S and Black, P M. A phase I trial of a new recombinant human beta-interferon (BG9015) for the treatment of patients with recurrent gliomas. (1997). Clinical Cancer Research 3(3): 381–7

Hall A and Rumack B. Hydroxycobalamin/sodium thiosulfate as a cyanide antidote. (1987). Journal of Emergency Medicine 5(2):115–121.

Komanduri, S and Cotler, S J. Hepatitis C. (2002). Clinical Perspectives in Gastronenterology. March/April 2002 issue p91–99.

Miller D H. Magnetic resonance in monitoring the treatment of multiple sclerosis. (1994). Annals of Neurology 36: Suppl :S91–4.

Mizoule J. Etude de l'Action de l'Hydroxocobalamine a l'Egard de l'Intoxication Cyanhydrique [Thesis]. (1966). Faculte de Pharmacie de l'Universite de Paris, pp. 1–178. Cited In: Hall and Rumack., 1987.

Nishizawa Y, Yamamoto T, Terada N, Fushiki S, Matsumoto K and Nishizawa Y. Effects of methylcobalamin on the proliferation of androgen-sensitive or estrogen-sensitive malignant cells in culture and in vivo. (1997). International Journal of Vitamin Nutrition Research 67(3): 164–170

Nyland H, Myhr K M, Lillas F, Smievoll A I, Riise T, Nortvedt M and Nilsen R. Treatment of relapsing-remittent multiple sclerosis with recombinant human interferon-alfa-2a: design of a randomised, placebo-controlled, double blind trial in Norway. (1996) Multiple Sclerosis 1(6):372–5

Pouly S and Antel J P. Multiple sclerosis and central nervous system demyelination. (1999). Journal of Autoimmunity 13: 297–306.

Poydock M. Inhibiting effect of vitamins C and B12 on the mitotic activity of ascites tumors. (1979). Experimental and Cellular Biology 47:210–217.

Poydock M E, Harguindey S, Hart T, Takita H and Kelly D. Mitogenic inhibition and effect of survival of mice bearing L1210 leukemia using a combination of dehydroascorbic acid and hydroxycobalamin. (1985). American Journal of Clinical Oncology 8(3):266–269.

Lott W B, Takyar S S, Tuppen J, Crawford D H, Harrison M, Sloots T P and Gowans E J. Vitamin B12 and hepatitis C: molecular biology and human pathology. (2001). Proceedings of National Academy of Sciences 98(9): 4916–4921

Sakane T, Takada S, Kotani H and Tsunematsu T. Effects of methyl-B12 on the in vitro immune functions of human T lymphocytes. (1982). Journal of Clinical Immunology 2(2): 101–109

Shimizu N, Hamazoe R, Kanayama H, Maeta M and Koga S. Experimental study of anti-tumor effect of methyl-B12. (1987). Oncology 44(3): 169–173

Steinman L, Lindsey J W, Alters S and Hodgkinson S. From treatment of experimental allergic encephalomyelitis to clinical trials in multiple sclerosis. (1993). Immunology Series 59: 253–60

Tamura J, Kubota K, Murakami H, Sawamura M, Matsushima T, Tamura T, Saitoh T, Kurabayshi H and Naruse T. Immunomodulation by vitamin B12: augmentation of CD8+ T lymphocytes and natural killer (NK) cell activity in vitamin B12-deficient patients by methyl B12 treatment. (1999). Clinical and Experimental Immunology 116(1): 28–32

Tsao C, Miyashita K and Young M. Cytotoxic activity of cobalamin in cultured and nonmalignant cells. (1990) Pathobiology 58:292–296.

Watanabe T, Kaji R, Oka N, Bara W and Kimura J. Ultra-high dose methylcobalamin promotes nerve regeneration in experimental acrylamide neuropathy. (1994) Journal of Neurological Sciences 122(2): 140–143.

Weinberg J B, Sauls D L, Misukonis M A and Shugars D C. Inhibition of productive human immunodeficiency virus-1 infection by cobalamins. (1995). Blood. 86(4):1281–1287

Weinberg J B, Shugars D C, Sherman P A, Sauls D L and Fyfe J A. Cobalamin inhibition of HIV-1 integrase and integration of HIV-1 DNA into cellular DNA. (1998). Biochemical Biophysical Research Communications 246(2): 393–397

We claim:

1. A method of treating a viral disease comprising the step of administering to a patient a pharmaceutical composition comprising:

(i) hydroxocobalamin; and
(ii) at least one interferon compound selected from the group consisting of interferon alpha and interferon beta.

2. The method of claim 1 wherein the disease being treated is hepatitis B infection.

3. The method of claim 1 wherein the disease being treated is hepatitis C infection.

4. A method of treating a viral disease comprising the steps of administering to a patient, either together, or separately:

(i) hydroxocobalamin; and
(ii) at least one interferon compound selected from the group consisting of interferon-alpha and interferon-beta.

5. The method of claim 4 wherein said interferon compound is interferon-beta.

6. The method of claim 1 wherein the dose of hydroxocobalamin is between 10–2500 mg daily.

7. The method of claim 5 wherein the dose of hydroxocobalamin is between 10–2500 mg daily.

8. The method of claim 1 wherein the dose of the interferon compound is equivalent to the therapeutic dose range of said interferon compound when used alone.

9. The method of claim 1 wherein the dose of the interferon compound is less than the therapeutic dose range of said interferon compound when used alone.

10. The method of claim 4 wherein the dose of hydroxocobalamin is between 10–2500 mg daily.

11. The method of claim 4 wherein the dose of the interferon compound is equivalent to the therapeutic dose range of said interferon compound when used alone.

12. The method of claim 4 wherein the dose of the interferon compound is less than the therapeutic dose range of said interferon compound when used alone.

13. The method of claim 4 wherein said interferon compound is interferon-alpha.

14. The method of claim 1 wherein said interferon compound is interferon-alpha.

15. The method of claim 1 wherein said interferon compound is interferon-beta.

16. The method of claim 4 wherein the disease being treated is hepatitis B infection.

17. The method of claim 4 wherein the disease being treated is hepatitis C infection.

* * * * *